United States Patent [19]

Blackborow et al.

[11] Patent Number: 5,616,654
[45] Date of Patent: Apr. 1, 1997

[54] POLYOLEFIN DIOLS

[75] Inventors: John R. Blackborow, Edinburgh, Scotland; Lee J. Morton, Hull, England

[73] Assignee: BP Chemicals Limited, London, England

[21] Appl. No.: 680,011

[22] Filed: Jul. 15, 1996

Related U.S. Application Data

[62] Division of Ser. No. 462,010, Jun. 5, 1995.

[30] Foreign Application Priority Data

Apr. 10, 1995 [GB] United Kingdom .................. 9507393

[51] Int. Cl.$^6$ ........................................................ C08F 8/06
[52] U.S. Cl. ........................ 525/333.7; 525/337
[58] Field of Search ........................................... 525/333.7

[56] References Cited

U.S. PATENT DOCUMENTS 4,316,973  2/1982  Kennedy .............................. 525/333.7

FOREIGN PATENT DOCUMENTS 9010022  9/1990  WIPO .

OTHER PUBLICATIONS

Ivan et al, J. Polymer Science, vol. 18, pp. 3177–3191, (1980).

*Primary Examiner*—Bernard Lipman
*Attorney, Agent, or Firm*—Brooks Haidt Haffner & Delahunty

[57] ABSTRACT

This invention relates to a process for the production of polyolefin 1,3-diols, said process comprising (a) reacting a polyolefin epoxide with a borane or a precursor thereof in a borane-co-ordinating solvent to form an intermediate borane ester, and (b) subjecting the intermediate borane ester so formed in (a) to an alkaline oxidative hydrolysis to form the polyolefin diol. 1,3-diols of polyolefins, especially those of atactic polypropylene and poly(iso)butene, having a —C(CH$_3$)=CH$_2$ end group are novel compounds. These diols can be converted into useful products such as e.g. the corresponding carboxylic acids, diamines or hydroxyamines, or polyethers which are useful as such or as intermediates for producing lube oil and fuel additives.

2 Claims, No Drawings

POLYOLEFIN DIOLS

This application is a division of application Ser. No. 08/462,010 filed on Jun. 5, 1995 for which the benefits of priority are claimed under 35 U.S.C. §120.

This invention relates to novel polyolefin 1,3-diols, specifically polybutene 1,3-diols and to a method for the preparation of such polyolefin diols.

It is well known from Ivan, B et al in the Journal of Polymer Science. 18, pp 3177 et seq. (1980) to convert polyisobutene having only terminal vinylidene unsaturation to the corresponding primary alcohol by hydroboration thereof with borane tetrahydrofuran followed by subsequent cleavage in the presence of an alkali and an oxidising agent to give the corresponding primary mono-alcohol.

It is also known from our earlier published EP-A-0468996 to convert polyisobutenes to the corresponding carbonyl compounds by epoxidation with a peroxygen compound followed by an acid catalysed isomerisation thereof. The carbonyl compound so formed is an aldehyde when the polyisobutene has terminal vinylidene groups. Such aldehydes can also be converted to the corresponding polyisobutenyl primary alcohols by hydrogenation. However, the products resulting from the acid catalysed isomerisation of the epoxide is a mixture of aldehydes (from the epoxides of the terminal olefins), ketones, polybutene and the corresponding dienes, the latter being formed by elimination of water or methanol from the epoxides of non-terminal polyolefins. The hydrogenation of a mixture of such products leads to a mixture of products comprising substantially mono-alcohols.

Neither of the above processes lead to polyolefin 1,3-diols.

It has now been found that polyolefin 1,3-diols can be made by subjecting the polyolefin epoxides, especially those epoxides which have polyolefin chains substituted with one or more alkyl groups on the olefin carbon atoms in addition to the polyolefin chain, to a reaction with a borane in a borane-co-ordinating solvent which may be an ether such as tertrahydrofuran to form an ester and subsequent oxidative cleavage thereof to form the 1,3-diol.

Accordingly, the present invention is a process for the production of polyolefin 1,3-diols, said process comprising:

a. reacting a polyolefin epoxide with a borane or a precursor thereof in a borane-co-ordinating solvent to form an intermediate borane ester, and b. subjecting the intermediate borane ester so formed in (a) to an alkaline oxidative hydrolysis to form the polyolefin 1,3-diol.

By the expression "borane" is meant here $BH_3$ or $RBH_2$ wherein R is an alkyl or an aryl group. Such boranes may be produced in situ by using a combination of a borohydride and an acid which is thus the precursor to a borane.

By the expression "polyolefin diol" is meant here and throughout the specification a polyolefin dihydric alcohol, whether they be primary, secondary or tertiary dihydric alcohols.

The polyolefin expoxide is suitably a polybutene epoxide and such compounds are already described in our published EP-A-0468966. Thus, any polyolefin (optionally with suitable substituents) which has a molecular weight in the range from 300 to 3000 as determined by vapour pressure osmometry (hereafter VPO) can be used to form the epoxide. The unsaturation in the polyolefin used may be in the terminal position or in an internal position, but is preferably in the terminal position, i.e. the polyolefin chain is terminated by a $-C(CH_3)=CH_2$ group. Polymers terminating in a $-C(CH_3)=CH_2$ group are the so called "high vinylidene polyolefins". Specific examples of polyolefins that may be used include polypropylene, especially atactic polypropylene and polybutene. Diols, especially the 1,3-diols, derived from polyolefins having a $-C(CH_3)=CH_2$ end group in their structure are novel.

In this context, the term "polybutene" as used herein and throughout the specification is meant to embrace poly(iso)butenes because the latter are usually produced from hydrocarbon feedstock such as e.g. a butadiene raffinate which is a mixture of n-butenes and iso-butene. These polybutenes preferably, though not necessarily, have at least 50% of their unsaturation in the terminal position, i.e. they terminate in a $-C(CH_3)-CH_2$ group and are also known as 'high vinylidene polybutenes'. Polybutenes of this type are, for instance, described in our published EP-A-145235. These polybutenes usually have a molecular weight in the range of 250–5000. Such polybutenes are commercially available as ULTRAVIS® (ex BP Chemicals Ltd).

The polyolefins can be suitably epoxidised using a peroxygen compound such as e.g. m-chloro perbenzoic acid, hydrogen peroxide or mixtures thereof with sulphuric acid, or tertiary butyl peroxide in the presence of a molybdenum catalyst.

The epoxidation is suitably carried out using a solution of the polyolefin in a solvent inert under the reaction conditions such a chlorohydrocarbon e.g. dichloromethane or carbon tetrachloride. The epoxidation reaction is suitably carried out at ambient temperature and pressure, preferably at temperatures below 40° C. It is generally not necessary to purify or isolate the epoxidation products unless the decomposition products from the peroxygen compounds used for epoxidation are undesirable or detrimental to the epoxide.

Such methods are described in our published EP-A-0468966 referred to above and are incorporated herein by reference.

The epoxidised polyolefin is reacted with a borane, preferably $BH_3$, in a borane-co-ordinating solvent which may be an ether such as e.g. tetrahydrofuran, 1,4-dioxane, a dialkyl ether, a diaryl ether or an alkyl aryl ether. The amount of borane used on a mole/mole basis is suitably in the range from 0.8 to 2.5, preferably from 1 to 2.0 of the polyolefin epoxide. The borane in ether solution used is suitably in the range from 0.001 to 10 molar, preferably from 0.5 to 5.0 molar. This reaction is suitably carried out in the presence of one or more solvents inert under the reaction conditions such as e.g. toluene or tetrahydrofuran. The reaction is also carded out in an atmosphere, such as e.g. nitrogen, which is inert under the conditions. The reaction with the borane is best conducted at temperatures from slightly below ambient up to 50° C. due to the slightly exothermic nature of the reaction of the epoxide with the borane. This reaction is suitably carried out over a duration ranging from about 10 minutes to about 10 hours, preferably about 1.5 to 7.5 hours, with continuous stirring. Completion of the reaction may be signified by a fall in the reaction temperature. At this stage, the reaction mixture is diluted with a volume of a solvent containing hydroxyl groups, such as e.g. water, an alcohol or a glycol, which is normally immiscible with the reaction medium, then vigorously agitated and then allowed to settle into aqueous and organic phases. The organic phase is recovered and after additional water washing thereof in several stages, the aqueous phase is discarded whereas the organic phase, which may be in the form of an emulsion, is collected, combined and demulsfied, if necessary using an emulsion breaker, and then dried e.g. over anhydrous magnesium sulphate. This dried solution in an organic solvent contains the borated derivative of the polyolefin epoxide.

The products from step (a) comprising the borated derivative of epoxidised polyolefin is converted to the corresponding diol by an alkaline oxidative hydrolysis step (b). This step involves suitably heating the borated derivative of the polyolefin epoxide to moderately high temperatures such as e.g. above 45° C., preferably from 50° C.–75° C. in order to obtain a homogeneous solution in a solvent which may be an ether or a mixture of an ether and a hydrocarbon. The homogeneous solution is then reacted with continuous stirring with an aqueous solution of an oxidising agent, such as e.g. hydrogen peroxide, in the presence of an aqueous alkali, such as e.g. an aqueous sodium hydroxide solution. The amount of oxidising agent used on a mole/mole basis is suitably in the range from I to 100, preferably from I to 10 based on the polyolefin epoxide reactant. The amount of alkali used on a mole/mole basis is suitably in the range from 1 to 100, preferably from 1 to 10 based on the polyolefin epoxide. This reaction is carried out by gentle addition of alkali and the oxidising agent together or separately dropwise into the reaction over a period of time suitably over a duration of e.g. 15 minutes to 3 hours, preferably a duration of 45 minutes to 1.5 hours. Thereafter the reaction is continued with stirring for a further period of 1–10 hours, preferably 0.5–6 hours. The reaction mixture is then allowed to separate again into aqueous and organic phases. The organic phase is recovered and washed several times with water and then extracted with an aliphatic hydrocarbon solvent such as e.g. n-heptane. The n-heptane solution is then dried and then the solvent removed to obtain the desired polybutene diol.

It is not necessary to isolate the intermediate borane ester product from step (a) before proceeding with step (b). After completion of step (a) as described above, the reaction mixture can be raised to a temperature of 45° C. or above and may then be subjected directly to an alkaline oxidative hydrolysis step (b) in order to obtain the desired polybutene diol.

The process is particularly suited to the production of 2-polybutenenyl-1,3-diol which is a novel compound and is obtained in high yield (>80%).

This process has several advantages over the prior art processes. These are:

i. The process can produce polyolefin monohydric diols which may be primary, secondary or tertiary unlike the Ivan et al process referred to above which can only produce a primary mono-alcohol.

ii. The process can use relatively impure and commercial feedstock such as e.g. Raffinate I in order to produce the polyolefin epoxide whereas the Ivan et al process referred to above has to use relatively pure feedstock comprising purely of high vinylidene polyolefins.

iii. The process does not suffer from the disadvantages of having to convert the polyolefin epoxide first into an aldehyde by isomerisation before being subjected to hydrogenation in order to obtain alcohols.

iv. The process can use relatively impure polyolefin epoxides for reaction with borane in the presence of an ether.

The polyolefin diols of the present invention can be convened into useful products such as e.g. the corresponding carboxylic acids, diamines or hydroxy-amines, or polyethers. Diamines or hydroxy-amines can be prepared from the diols by methods known in the art such as e.g. by:

i. Reaction with hydrogen and amines over a Raney nickel catalyst (J Org Chem, 50(20), 3713–3721 (1985);

ii. Reaction with an amine over a CuO, Cr2O3, Na2O catalyst (Tetrahedron Letters. pp. 1937 ( 1977);

iii. Reaction with an amine and hydrogen over a CuO catalyst (Synthetic Communications, 8, pp 27 (1978); and iv. Reaction with an amine over an aluminium tert-butoxide and a Raney nickel catalyst (Synthesis, pp 722 (1977).

The polybutene diols can be converted by dehydration, e.g. with sulphuric acid, to the corresponding polybutene polyethers by intermolecular dehydration.

Polyolefins such as polybutene with two acid or amino functions are particularly useful as intermediates in cross-linking reactions to produce lubricant or fuel additives. Thus polyisobutenyl malonic acid can be produced from polyisobutenyl diol by oxidation of the diol with an oxidising agent such as e.g. 50% nitric acid, vanadium pentoxide, potassium permanganate or the like well known in the art.

The present invention is further illustrated with reference to the following Example:

EXAMPLE 1

Polyisobutene epoxide (60 g, 0.06 mol) of Mn=1000 containing 1.6% oxygen and no residual olefinic unsaturation (as determined by $^{13}$C NMR analysis) was charged to a round-bottomed flask fitted with a reflux condenser, thermocouple, dropping funnel, nitrogen blanket and a mechanical stirrer. Toluene (60 g) was added and the mixture agitated until homogeneous. A solution of 1 mol/dm$^3$ borane in tetrahydrofuran (90 ml, 0.09 mol) was then added over two hours via the dropping funnel. During this period a temperature increase from 24° C. to 31° C. was observed. After a further four hours of agitation, the solution temperature returned to 25° C. Water (4.86 g, 0.27 mol) was added cautiously over one hour when vigorous foaming was observed. When the foaming had subsided, a further amount of water (100 g) was added. The resultant mixture was then agitated again for 30 minutes and was then allowed to separate into aqueous and organic phases. The aqueous phase was discarded and the organic phase was washed four times with water. The organic phase was then dried over anhydrous magnesium sulphate and filtered. The filtrate containing the borated derivative (Product A) of the polybutene epoxide was then stripped of the solvent at 120° C. to recover about 58 g of Product A.

An aliquot of Product A (10 g) together with tetrahydrofuran (25 g) was then charged to a round-bottomed flask fitted with a reflux condenser, a thermocouple, a dropping funnel and a magnetic stirrer. The mixture of Product A and tetrahydrofuran was heated to 50° C. and agitated until homogeneous. Hydrogen peroxide (12.3 g, 27.5% aqueous solution, 0.1 mol) and sodium hydroxide (12.3 g, 1 mol/dm$^3$ aqueous solution, 0.0123 mol) were added cautiously to the reaction mixture via the dropping funnel over one hour, left a further three hours under agitation and then allowed to separate into aqueous and organic phases. The upper organic phase was recovered and washed with water five times (5×100 g) and then extracted with n-heptane (25 g). The n-heptane solution was dried over anhydrous magnesium sulphate and vacuum stripped at 120° C. for two hours. A light yellow product was obtained which contained 2.6% oxygen and was characterised to be 2-polybutene-1,3-diol by $^{13}$C NMR spectroscopy.

We claim:

1. 1,3-diols of polyolefins having a —C(CH$_3$)=CH$_2$ end group.

2. 1,3-diols of polyolefins according to claim 1 wherein the polyolefin is atactic polypropylene or poly(iso)butene having a molecular weight in the range from 300 to 3000 as determined by vapour pressure osmometry.

* * * * *

UNITED STATES PATENT AND TRADEMARK OFFICE
CERTIFICATE OF CORRECTION

PATENT NO. : 5,616,654
DATED : April 1, 1997
INVENTOR(S) : JOHN R. BLACKBOROW et al It is certified that error appears in the above-indentified patent and that said Letters Patent is hereby corrected as shown below:

Col. 2, l. 10, formula should read "$-C(CH_3)=CH_2$"

Col. 3, l. 8, should read "from $\underline{1}$ to 100," and "from $\underline{1}$ to 10".

Signed and Sealed this

Eleventh Day of November, 1997

Attest:

BRUCE LEHMAN

Attesting Officer

Commissioner of Patents and Trademarks